United States Patent [19]

Orvik

[11] 4,275,212

[45] Jun. 23, 1981

[54] METHOD OF PREPARING PYRIDINYLOXYPHENOLS AND DERIVATIVES

[75] Inventor: Jon A. Orvik, Danville, Calif.

[73] Assignee: The Dow Chemical Company, Midland, Mich.

[21] Appl. No.: 93,646

[22] Filed: Nov. 13, 1979

Related U.S. Application Data

[63] Continuation-in-part of Ser. No. 824,377, Aug. 15, 1977, abandoned.

[51] Int. Cl.$^3$ .................. C07D 213/63; C07D 213/68
[52] U.S. Cl. ........................................ 546/290; 71/94; 546/261
[58] Field of Search ................... 260/297 R; 546/290, 546/261

[56] References Cited

U.S. PATENT DOCUMENTS

| | | | |
|---|---|---|---|
| 3,637,720 | 1/1972 | Nishiyama et al. | 546/300 |
| 3,716,549 | 2/1973 | Darsow et al. | 546/296 |
| 4,046,553 | 9/1977 | Takahashi et al. | 546/261 |

OTHER PUBLICATIONS

Klingsberg, Pyridine and Its Derivatives, Part Three, pp. 571, 576 and 678, Interscience Publishers, 1962.

*Primary Examiner*—John D. Randolph
*Attorney, Agent, or Firm*—Edward E. Schilling; Ronald G. Brookens

[57] ABSTRACT

Pyridinyloxphenol compounds and derivatives are prepared by reacting a 2(6)- or 4-substituted pyridine intermediate with a hydroquinone reactant and a base, an excess molar amount of base as compared to the molar amount of hydroquinone reactant being employed along with a requisite reaction temperature whereby there is formed no more than 10 mole percent of undesired 1,4-(bis(pyridinyloxy))benzene by-product after no more than about 8 hours. Treatment of the undesired by-product in a similar manner alone or by isolation and recycling in the process also results in substantial conversion of said by-product to the desired mono pyridinyloxphenol compound.

24 Claims, No Drawings

METHOD OF PREPARING PYRIDINYLOXYPHENOLS AND DERIVATIVES

CROSS-REFERENCE TO RELATED APPLICATIONS

This application is a continuation-in-part of Application Ser. No. 824,377, filed Aug. 15, 1977 and now abandoned.

BACKGROUND OF THE INVENTION

The present invention concerns the improved preparation of pyridinyloxyphenol compounds by reaction of a 2(6)- or 4-substituted pyridine intermediate with a hydroquinone reactant in the presence of an excess amount of a base. The invention also concerns the conversion of bis(pyridinyloxy)benzene compounds to the desired pyridyloxyphenol compounds by similar treatment with a hydroquinone and excess base.

The reaction of 2(6)-substituted pyridine compounds with a hydroquinone and an alkaline material to form correspondng substituted pyridinyloxyphenol compounds (hereinafter collectively referred to for convenience as "POP" compounds), useful as herbicides, is disclosed in abstracts of Japanese Patent Application Nos. SHO-50-29556 and SHO-49-118676, and by U.S. Pat. No. 4,046,553 issued Sept. 6, 1977, which is based on both said patent applications.

However, it has now been discovered that the direct use of a hydroquinone reactant suffers from disadvantages in that significant amounts, e.g., as much as 25–50% or more of the expected desired product yield; of undesired bis(pyridinyloxy)benzene compounds (hereinafter collectively referred to as "bis by-products") are formed, thus detrimentally affecting product yield and quality as well as manufacturing economics. The formation of one such by-product (I) with the desired product (II) is illustrated by the following reaction sequence:

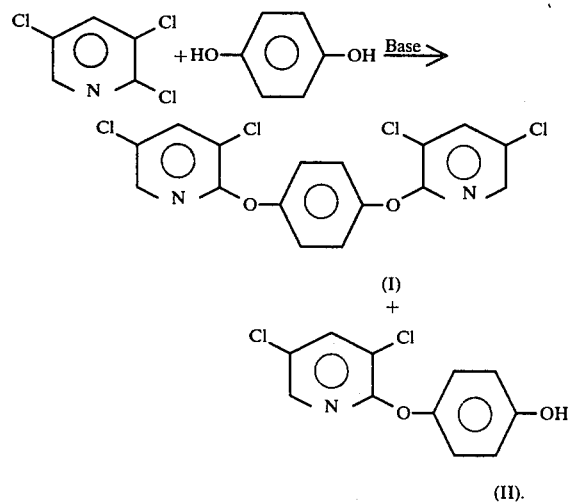

Accordingly, it is an object of the present invention to provide an improved method for producing pyridinyloxyphenol compounds without the significant production of undesired bis by-products.

It is also an object of the present invention to provide a novel method for the conversion of undesired "bis by-products" to the desired pyridinyloxyphenol derivatives, when treated alone or in the context of recycling in the production of the desired POP derivatives starting with 2(6)- or 4-substituted pyridine and hydroquinone.

SUMMARY OF THE INVENTION

The present invention is an improvement in the process for preparing pyridinyloxyphenol compounds by reacting a 2(6)- or 4-substituted pyridine reactant optionally having additional ring substituents with a hydroquinone in the presence of a base material under an inert atmosphere and an inert reaction medium, the improvement comprising adding the base material over at least a ½ hour period and preferably over not more than a 1½ hour period and utilizing the requisite reaction temperature and molar ratio of base to hydroquinone to form less than about 10 mole percent of bis by-product in about 8 hours, the reaction temperature being in the range of about 50° to about 130° C. and the molar ratio being in the range of about 1.5:1 to about 2:1. The improved process provides for surprisingly rapid transformation of the undesired bis by-product initially formed to POP compound and improves the yield of the POP compound.

The present invention also concerns a process for converting said bis by-product, to the desired corresponding POP compound, said process comprising reacting said bis by-product with the requisite hydroquinone reactant, i.e., having the same oxygen bridge configuration as the phenyl moiety of the bis by-product, ortho, meta or para, and, a base, said base and hydroquinone reactant being employed in a molar ratio and at a reaction temperature sufficient to convert a substantial amount of the bis(pyridinyloxy) benzene by-product to the corresponding pyridinyloxyphenol compound whereby no more than about 10 mole percent, more preferably no more than 5 mole percent and most preferably no more than 0.5 mole percent remains after about 8 hours and preferably after about 2 hours. The invention also contemplates operating under circumstances that less than all bis by-product is transformed into POP compound, but is isolated and recycled in the reaction process and the requisite hydroquinone and base added to the reaction mixture to achieve substantial conversion to POP compound with less than about 10 mole percent bis by-product remaining after up to about 8 hours and more preferably lesser amounts and in less time as recited above for conversion of bis by-product.

DETAILED DESCRIPTION OF THE INVENTION

In carrying out the process of preparing POP compounds, the selected pyridine and hydroquinone reactants are contacted under an inert atmosphere, e.g., nitrogen, and in the presence of an inert carrier medium, such as, for example, dimethylsulfoxide (DMSO). A base material such as, for example, sodium or potassium hydroxide, trimethylammonium hydroxide, or similar strong base material, is added to the reaction mixture to bring about reaction. It is so highly preferred as to be practically essential that the base material be added slowly, whether continuously or portionwise over at least about a ½ hour period and preferably over not more than about a 1½ hour period, so that formation of a precipitate in the reaction mixture is avoided or minimized.

A sufficient molar ratio of base:hydroquinone is employed along with the requisite reaction temperature to minimize the undesired production of bis by-product after about 8 hours from the start of the base addition to about 10 mole % or less based on reaction product yield and more preferably after 2 hours. In a more preferred embodiment, sufficient said molar ratio and reaction temperature are employed to form less than about 5 mole % bis by-product in less than about 8 hours and preferably less than about 2 hours. Most preferably less than 0.5 mole % bis by-product is formed after about 8 hours and preferably after about 2 hours. The molar ratio of base to hydroquinone reactant must be at least about 1.5:1. A more preferred ratio is from about 1.7:1 to about 2:1, with about a 2:1 molar ratio being most preferred as this results in more complete and prompt conversion of the bis by-product to POP compound.

The reaction mixture is subsequently maintained, after base addition and with agitation, at ambient pressures and at a temperature of from about 50° to about 130° C., preferably about 70° to about 130° C., and most preferably about 100° C., for a period of from about 2 hours to about 8 hours from the start of the base addition and the desired POP product then recovered according to conventional techniques. Elevated pressures may be advantageous with certain volatile carrier media. Further treatment of the POP product can also be carried out according to known techniques, such as described in said U.S. Pat. No. 4,046,553, to react the free hydroxy group with the requisite reactants to form biologically active compounds, e.g., pyridinyloxy phenyl, alkyl ethers or pyridinyloxyphenoxy alkanoic acids.

It is essential that the pyridine reactant have, in the ring position alpha to the nitrogen, i.e., in the 2- or 6-position depending on numbering and herein sometimes written "2(6)", or in the 4 position, a substituent which is reactive with the OH function of the hydroquinone reactant. The most practical and preferred of the suitable substituents are the halogens, fluorine, chlorine, bromine and iodine, in addition to alkylsulfonyl in which alkyl may be a relatively large group but for practical reasons is normally methyl. The preferred halo substituents on account of cost are chloro and bromo with chloro most preferred.

While the 2(6) and 4 ring positions are of significance with respect to chemical reactivity in the present process, the 3 and/or 5 positions are most significant with respect to biological activity of the compounds eventually made from the phenols made according to the instant process. The present process is effective regardless of the presence or absence of such additional substituents. The additional substituents, which impart biological activity to compounds formed by reaction of haloalkanoic acids with the presently described POP compounds, are lower alkyl having 1 to 3 carbons, preferably methyl; trifluoromethyl, particularly active in the 5 position; and any of the halogens, preferably chloro or bromo.

Suitable pyridine reactants include 2-chloropyridine, 2-bromopyridine, 2-fluoropyridine, 2-iodopyridine, 2-(methylsulfonyl)pyridine, 4-chloropyridine, 4-bromopyridine, 4-(methylsulfonyl)pyridine, 2,3,5-trifluorochloropyridine, 2-chloro-5-trifluoromethylpyridine, 2-(methylsulfonyl)-5-trifluoromethyl pyridine, 2,3-dichloro-5-trifluoromethyl pyridine and 3,5-dibromo-2-chloropyridine. Preferred pyridine reactants include 2,3,5-trichloropyridine, 2-chloro-5-trifluoromethylpyridine and 2,3-dichloro-5-trifluoromethyl pyridine. The molar ratio of pyridine reactant to hydroquinone reactant ranges from about 1:1 to about 1:3. Preferably a molar ratio of about 1:1 is employed as this minimizes the need to recover excess hydroquinone from the reaction mixture. Preferably, an excess mole ratio of base to pyridine reactant is also used. The actual amounts of all the reactants to be employed will depend upon the initial amount of pyridine reactant employed and will be readily apparent to those skilled in the art. Inert reaction media which can be employed herein include dimethylsulfoxide and other similar media. Preferred POP compounds include 4-(3,5-dichloro-2-pyridinyloxy)phenol, 4-(5-trifluoromethyl-2-pyridinyloxy)phenol and 4-(3-chloro-5-trifluoromethyl-2-pyridinyloxy) phenol.

Reactive 2(6)- or 4-substituted pyridine compounds having additionally a trifluoromethyl group in the 5-position have been found to form POP compound more rapidly than other reactive 2(6)- or 4-substituted pyridines, particularly the halopyridines, with or without other substituents such as halo in the 3 and/or 5 ring position. Thus, product can be formed with a low level of bis by-product in less than about 1 hour when up to about 2 hours is often required on starting with other reactive pyridines.

Hydroquinone reactants which can be employed in the present invention include, for example, hydroquinone (p-dihydroxyphenol), o- and m-hydroquinones, which can have a lower alkyl such as a methyl substituent on the ring, if desired. Hydroquinone, i.e., p-hydroxyphenol is a preferred reactant.

The process whereby the undesired bis(pyridinyloxy)benzene by-products are converted to the corresponding POP compounds is carried out by reacting the bis by-product with the corresponding hydroquinone (generally about equimolar amounts) and base materials, under conditions, including base to hydroquinone molar ratio requirements as set forth hereinabove for the reaction of a pyridine reactant and a hydroquinone reactant, in an inert carrier medium, except that substantial conversion is achieved with as little as about 1:1 base to hydroquinone molar ratio in the substantial absence of reactive 2(6)- or 4-substituted pyridine. Conveniently, the reaction mixture portion remaining after separation of the desired POP product and containing the bis by-product can be directly used in the present process without further treatment. Treatment of the bis by-product in the absence of the reactive pyridine according to the process of the present invention can result in the conversion of about 80 mole percent or more of the bis by-product treated with up to about 99 mole percent thereof being converted to the desired POP compound, at higher molar ratios and temperatures such as 100° C., some small amounts of pyridinol being generally formed. Preferably, at least about 95 mole percent or more, most preferably at least about 99 mole percent, of the bis by-product is converted to the desired POP compound. Generally, it has been observed that use of higher molar amounts of base to hydroquinone and higher temperatures gives the desired conversion rates in the preferred time periods of up to 8 hours, or more preferably up to 2 hours, as well as higher conversion to the desired POP product than with about equimolar amounts. Accordingly, it is preferred that the base and hydroquinone materials be employed in molar ratios sufficient to give at least about 90 mole percent conversion of the bis by-product to the desired POP compound. Base to hydroquinone molar ratios of from about 1:1 to about 2:1, more preferably about 1.7:1 to about 2:1 are employed. In the most preferred embodiment, a molar ratio of base to hydroquinone of about 2:1 is employed. In another preferred embodiment, about 99 mole percent or more of the bis by-product is converted to the desired POP compound and related products, the objective being to form product with no more than about 0.5 mole percent of bis by-product therein. Also, it is preferred that the base addition be carried out portionwise or at least slowly as noted above. DMSO is a preferred carrier medium for this embodiment. The actual amounts of base and hydroquinone to be employed will be readily apparent to those skilled in the art.

The followng reaction sequence is illustrative of this embodiment:

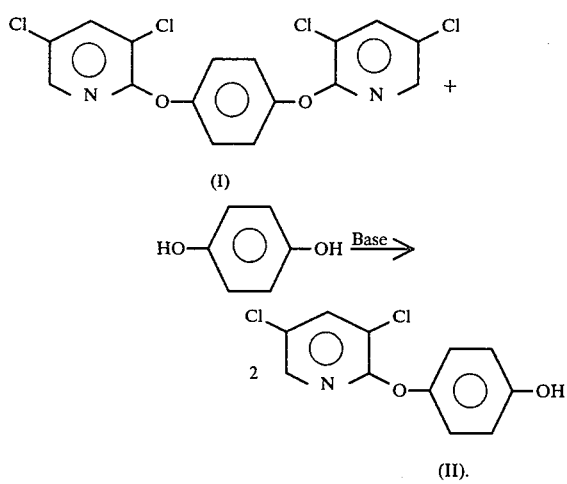

In a further embodiment of the process of the invention the reactive pyridine and the hydroquinone reactant are reacted in the presence of base under the conditions set forth above except the time of reaction, is shorter than required for conversion of most or all of the bis by-product to POP compound. The reaction mixture being strongly basic, the POP compound is in salt form and on addition of water the bis by-product can be extracted readily with a suitable solvent such as toluene, hexane or heptane. The POP compound, relatively free of bis by-product, is recovered from the aqueous-DMSO phase by methods well understood in the art for recovery of phenols, e.g., by acidification, solvent extraction, and flashing off of solvent. The bis by-product is then recovered from the solvent, e.g., by flashing off the solvent under reduced pressure conditions and the isolated bis by-product is recycled by addition to a reaction mixture of the requisite corresponding reactive pyridine and hydroquinone reactant, and, base material as described above, the proportions of base material and hydroquinone material being adjusted to provide a mole ratio within one of the ranges recited hereinabove and the recycle reaction procedure, if desired, being carried out repeatedly on a batch or continuous basis.

In the foregoing procedure the requisite corresponding reactive pyridine is a 2(6)- or 4-substituted pyridine having a halogen or a methylsulfonyl group on the ring at the point of attachment of phenoxy in the bis by-product and additionally, the same remaining ring substituents as the pyridinyl ring in the bis by-product. The corresponding hydroquinone reactant is a hydroquinone with the —OH groups in the same relative ortho, meta or para position as the oxygen bridges in the bis by-product.

To further illustrate the processes of the present invention, the following examples are provided. However, it should be understood that the details thereof are not to be regarded as limitations, as they may be varied as will be apparent to those skilled in the art.

EXAMPLE 1

About 4.02 grams (0.01 mole) of 1,4-((bis-(3,5-dichloropyridinyl)oxy))benzene, 1.10 grams (0.01 mole) of hydroquinone (p-hydroxyphenol) and about 1.5 grams of o-terphenyl (used as an internal standard for gas chromatograph analysis method) were mixed with 20 mls of dimethylsulfoxide (DMSO) and the resulting mixture was heated, under nitrogen and ambient pressures, to about 100° C. until the bis compound was dissolved. 0.80 Grams (0.01 mole) of 50% NaOH hydroxide was added portionwise with stirring and the resulting solution heated at about 100° C. for a period of about 270 minutes. A sample was then taken for analysis (the bis-by-product being soluble in organic phase while POP compound can be extracted with water) and another 0.8 grams (0.01 mole) of 50% NaOH was added to the reaction mixture which was then heated for about 100 minutes before another sample for analysis by gas chromatographic methods was taken.

As a result of such operations, it was found that treatment of the bis compound with equimolar amounts of base and hydroquinone and in the absence of halopyridine resulted in about 84% conversion of the bis compound to the corresponding 4-(3,5-dichloro-2-pyridinyloxy)phenol. Treatment wth a base:hydroquinone ratio of 2:1 was found to give about 100% conversion of the bis reactant with about 94% selectivity as to the desired 4-(3,5-dichloro-2-pyridinyloxy)phenol reactant.

EXAMPLE 2

In procedures similar to those in Example 1 above, except that a 2,3,5-trichloropyridine was used in place of the bis reactant, it was found that reaction of equimolar amounts of the pyridine reactant, hydroquinone and 50% NaOH in dimethylsulfoxide (DMSO) at 100°–116° C. for about 1½ hours gave product yields of 33% 1,4-((bis(3,5-dichloro-2-pyridinyl)oxy))benzene and about 49% of the desired mono compound, i.e., 4-(3,5-dichloro-2-pyridinyloxy)phenol. Reaction of 0.1 mole of the pyridine reactant with 0.2 mole of the hydroquinone and 0.15 mole of the 50% NaOH (added portionwise to the reaction mixture over a period of about 20 minutes) in 80 ml of DMSO at 90°–100° C. for about 5.5 hours resulted in a product yield of about 16.6% of the bis compound named above and about 75.9% of the desired mono compound. Further operations using equimolar amounts of pyridine reactant to hydroquinone reactant (0.4 mole each) and a mole ratio of base to hydroquinone of 2:1 (0.8 mole 50% caustic, 0.4 mole hydroquinone) in 250 ml of DMSO at temperatures of 100°–113° C. for about 2.5 hours resulted in a product yield of only 4% of the bis compound and 84.4% of the desired mono compound.

EXAMPLE 3

In each of a series of reactions carried out according to the present invention approximately 20 millimoles each of 2,3,5-trichloropyridine and hydroquinone (p-hydroxyphenol) accurately weighed and dissolved in about 20 ml of DMSO by heating were transferred to a reaction vessel and the resulting solution heated and maintained at about 100° C. under nitrogen at atmospheric pressure while sufficient 50% aqueous sodium hydroxide solution was added slowly with stirring until about 30, 34 and 40 millimoles respectively, of NaOH had been added over about a 1½ hour period, the amount of the base varying with respective runs.

After the base addition was complete, heating and stirring were continued and samples were drawn periodically and subjected to chromatographic analysis to determine the relative proportions of POP compound and bis by-product present.

The areas under the two respective peaks were computed and, using weight response curves, the apparent number of millimoles each of POP compound and bis by-product computed and then these values normalized using the total number of millimoles of pyridinyl moiety known to be added at the outset.

The sampling times from start of base addition and the number of millimoles of each of POP compound and bis by-product determined for each sampling time and the base:hydroquinone ratios employed are listed in the following table along with values for an additional run made by way of comparison in substantially the same manner but with a base:hydroquinone ratio of 1.19. After 380 minutes from the start of the base addition, during this last run, the temperature was raised to 145° C. and heating and stirring carried out for an additional 16.5 hours when a final sample was drawn and subjected to chromatographic analysis. Visual examination at that time showed that the reaction mixture had darkened indicating formation of degradation products.

TABLE
Course of Reaction of Halopyridine with Hydroquinone

| Run No. | Base:HQ Ratio | Time Min. | POP Compound Millimoles | BIS By-Product Milli-moles | Mole % |
| --- | --- | --- | --- | --- | --- |
| Comparison | 1.19:1 | 80 | 10.1 | 4.6 | 31 |
|  |  | 145 | 11.2 | 4.0 | 26 |
|  |  | 210 | 11.5 | 3.9 | 25 |
|  |  | 295 | 12.2 | 3.5 | 22 |
|  |  | 380 | 12.7 | 3.3 | 21 |
|  |  | 16.5 Hrs. (at 145° C.) | 16.4 | 1.4 | 8 |
| 1 | 1.52:1 | 90 | 11.8 | 3.5 | 23 |
|  |  | 150 | 13.4 | 2.7 | 17 |
|  |  | 210 | 14.9 | 2.0 | 12 |
|  |  | 270 | 15.6 | 1.6 | 9 |
| 2 | 1.72:1 | 90 | 15.2 | 1.9 | 11 |
|  |  | 155 | 18.2 | 0.4 | 2.2 |
|  |  | 225 | 18.5 | 0.3 | 1.6 |
|  |  | 275 | 18.7 | 0.2 | 1.0 |
|  |  | 430 | 18.9 | 0.1 | 0.5 |
| 3 | 2.05:1 | 90 | 18.8 | 0.1 | 0.5 |
|  |  | 150 | 19.0 | not detected | 0 |

HQ = hydroquinone (p-hydroxyphenol)
Time = time from start of base addition

The tabulated results show that at a reaction temperature of 100° C. and a base to hydroquinone ratio of about 1.2 the amount of bis by-product in the reaction mixture did not fall to 20 mole percent even after almost 6.3 hours while with a base to hydroquinone ratio of 1.5:1 the amount of bis by-product fell to 10 mole percent in less than 4.5 hours. With a molar ratio of 1.7:1 the amount of bis by-product was nearly down to 10 mole percent at first sampling while with the most preferred molar ratio of about 2:1 the amount of bis by-product was barely 0.5 mole percent at first sampling and not detectable after 2.5 hours.

It is also notable to observe that bis by-product obviously forms quickly initially and it is the transformation to POP compound which is time limiting.

EXAMPLE 4

The procedure of Example 3 was carried out using 2,3-dichloro-5-trifluoromethyl pyridine as the halopyridine and sufficient 50 weight percent aqueous sodium hydroxide to provide a 2.01:1 base to hydroquinone molar ratio on completing the base addition in 70 minutes. The amount of hydroquinone was very slightly in excess of the stoichiometric amount.

The reaction mixture in this case was sampled after 42 minutes from the start of the base addition when the molar ratio was 1.26:1 as well as at the completion of the base addition. Chromatographic analysis showed the following relative unit areas under the respective peaks:

| Sample Number | Hydroquinone | POP Compound | Bis By-Product |
| --- | --- | --- | --- |
| 1 | 12441 | 38,653 | 24,386 |
| 2 | 3087 | 65,686 | 0 |

The analysis indicates that a very substantial amount of bis by-product was formed initially which transformed to the POP compound so rapidly at higher base levels as not to be detectable at the end of the base addition.

This was confirmed by pouring the reaction mixture into about 100 ml. of water and observing a clear solution, whereas the bis by-product is not water soluble. Furthermore, the POP compound was recovered and recrystallized yielding white crystals melting at 78°–79° C., a temperature previously determined on crystalline material known to be the POP compound expected in this case, viz., 4-(3-chloro-5-(trifluoromethyl)pyridinyl-2-oxy)phenol.

Similar results are obtained with other bis by-products and with other reactive 2(6)- or 4-substituted pyridines and hydroquinone reactants.

What is claimed is:

1. In the process for preparing ring substituted or unsubstituted pyridinyloxyphenol compounds by reaction of a preselected reactive 2(6)- or 4-substituted pyridine reactant with about an equimolar amount of a preselected hydroquinone reactant in the presence of a base, the improvement which comprises: adding the base over a ½ hour to 1½ hour period and carrying out the said reaction at the requisite temperature and with the requisite molar ratio of base to hydroquinone reactant whereby product is formed in less than about 8 hours that contains less than about 10 mole percent of the corresponding bis(pyridinyloxy)benzene by-product, based on the weight of the desired pyridinyloxyphenol product formed, the reaction temperature being in the range of from about 50° to about 130° C. and the said molar ratio being in the range of from about 1.5:1 to about 2:1, and the reaction being carried out under an inert atmosphere and in an inert reaction medium.

2. The process of claim 1 wherein the requisite molar ratio and reaction temperature are employed to form less than about 5 mole percent by weight of bis(pyridinyloxy)benzene by-product.

3. The process of claim 1 wherein the requisite molar ratio and reaction temperature are employed to form less than about 0.5 mole percent of bis(pyridinyloxy)benzene by-product.

4. The process of claim 1 wherein the reaction is carried out at a temperature in the range of about 70° to about 130° C.

5. The process of claim 1 carried out at a temperature of about 100° C.

6. The process of claim 1 wherein the molar ratio of base material to hydroquinone reactant is in the range of about 1.7:1 to about 2:1.

7. The process of claim 1 wherein the molar ratio of base to hydroquinone is about 2:1.

8. The process of claim 1 wherein the product containing less than about 10 mole percent bis by-product is produced in about 2 hours.

9. The process of claim 2 wherein the product containing less than about 5 mole percent bis by-product is produced in about 2 hours.

10. The process of claim 1 wherein the pyridine reactant is 2,3,5-trichloropyridine, 2,3-dichloro-5-trifluoromethylpyridine or 2-chloro-5-trifluoromethylpyridine, and the hydroquinone reactant is p-dihydroxyphenol.

11. The process of claim 3 wherein the base is sodium hydroxide, the molar ratio of base to hydroquinone is about 2:1, the temperature of reaction is maintained at about 100° C.; and the low level of bis(pyridinyloxy)benzene is achieved in less than about 2 hours.

12. The process of claim 11 wherein the reactive pyridine has a —CF$_3$ group in the 5-position and the low level of bis(pyridinyloxy)benzene is achieved in less than about 1 hour.

13. The process of claim 11 wherein the pyridine reactant is 2,3,5-trichloropyridine, 2,3-dichloro-5-trifluoromethylpyridine or 2-chloro-5-trifluoromethylpyridine, and the hydroquinone reactant is p-dihydroxyphenol.

14. A process for preparing a substituted or unsubstituted pyridinyloxyphenol compound which comprises: reacting the requisite ring substituted or unsubstituted bis(pyridinyloxy)benzene reactant with about an equimolar amount of the requisite hydroquinone reactant having the same oxygen bridge configuration as the phenyl ring of the bis(pyridinyloxy) benzene reactant, in the presence of a base and substantially in the absence of reactive 2(6)- or 4-substituted pyridine, under an inert atmosphere and in the presence of an inert reaction medium, the base being added to the reaction mixture over about a ½ hour to about 1½ hour period and the reaction being carried out at the requisite temperature and with the requisite molar ratio of moles of base to the moles of added hydroquinone reactant whereby product is formed in less than about 8 hours that contains less than 10 mole percent of the bis(pyridinyloxy)benzene reactant, based on the weight of the desired pyridinyloxyphenol product, the reaction temperature being in the range of from about 50° to about 130° C. and the said molar ratio being in the range of from about 1:1 to about 2:1.

15. The process of claim 14 wherein the molar ratio of base to added hydroquinone reactant is in the range of about 1.5:1 to about 2:1.

16. The process of claim 15 wherein the molar ratio and temperature employed are sufficient that no more than about 5 mole percent of the bis(pyridinyloxy)benzene remains after about 2 hours of reaction time.

17. The process of claim 15 wherein the temperature and molar ratio employed are sufficient that no more than about 0.5 mole percent of the bis compound remains after about 2 hours reaction.

18. The process of claim 15 wherein the molar ratio of base material to hydroquinone reactant is in the range of about 1.7:1 to 2:1.

19. The process of claim 15 wherein the molar ratio of base to hydroquinone is about 2:1.

20. The process of claim 15 wherein the bis(pyridinyloxy)benzene compound is 1,4-(bis(3,5-dichloro-2-pyridinyloxy))benzene, 1,4-(bis(3-chloro-5-trifluoromethyl-2-pyridinyloxy))benzene or 1,4-(bis(5-trifluoromethyl-2-pyridinyloxy))benzene and the hydroquinone reactant is p-hydroxyphenol.

21. In the process for preparing ring substituted or unsubstituted pyridinyloxyphenol compounds by reacting a preselected reactive 2(6)- or 4-substituted pyridine with a preselected hydroquinone in the presence of a base under an inert atmosphere and in an inert reaction medium, the improvement which comprises: adding sufficient base to the reaction mixture over at least a 30 minute period while the reactants are maintained at about 50 to about 130° C. during and after the base addition to provide about 1.5 to about 2 moles of base per mole of hydroquinone, isolating the bis(pyridinyloxy) benzene by-product formed and, repeating the foregoing process, during which isolated bis(pyridinyloxy)benzene by-product is added to the reaction mixture along with the requisite hydroquinone, the hydroquinone being in an amount about equimolar to the by-product material added, and additional base added in an amount to provide a molar ratio of about 1.5:1 to about 2:1 to the sum of (a) moles of added hydroquinone plus (b) moles of by-product material added, the molar ratio being sufficient over-all for the formation of product containing less than 10 mole percent of bis(pyridinyloxy)benzene in less than 8 hours at the reaction temperature selected from commencement of the base addition.

22. The process as in claim 21 in which the molar ratio and the reaction temperature during repetition of the process are selected whereby there is formed less than 5 mole percent of bis(pyridinyloxy)benzene by-product in about 8 hours.

23. The process as in claim 22 in which the molar ratio and reaction temperature are selected whereby there is formed less than about 5 mole percent of said by-product in about 2 hours.

24. The process as in claim 23 in which the molar ratio and reaction temperature are selected whereby there is formed less than about 0.5 mole percent of said by-product in about 2 hours.

* * * * *

UNITED STATES PATENT AND TRADEMARK OFFICE
CERTIFICATE OF CORRECTION

PATENT NO. : 4,275,212

DATED : June 23, 1981

INVENTOR(S) : Jon A. Orvik

It is certified that error appears in the above—identified patent and that said Letters Patent is hereby corrected as shown below:

The first line in the abstract reading "Pyridinyloxphenol" should read -- Pyridinyloxyphenol --.

The last line in the abstract reading "pyridinyloxphenol" should read -- pyridinyloxyphenol --.

Column 1, line 6, reading "Applications" should read -- Application --.

Column 1, line 22, reading "correspondng" should read -- corresponding --.

Column 1, line 32, the semicolon should be changed to a comma.

Column 3, lines 64 and 65 reading "trifluorochloropyridine" should read -- trichloropyridine --.

Column 5, line 16, reading "followng" should read -- following --.

UNITED STATES PATENT AND TRADEMARK OFFICE
CERTIFICATE OF CORRECTION

PATENT NO. : 4,275,212
DATED : June 23, 1981
INVENTOR(S) : Jon A. Orvik

It is certified that error appears in the above—identified patent and that said Letters Patent is hereby corrected as shown below:

Column 6, line 37, reading "wth" should read -- with --.

Signed and Sealed this

First Day of December 1981

[SEAL]

Attest:

GERALD J. MOSSINGHOFF

*Attesting Officer*  *Commissioner of Patents and Trademarks*